United States Patent [19]

Nubel et al.

[11] Patent Number: 5,087,786
[45] Date of Patent: Feb. 11, 1992

[54] HALOGEN-ASSISTED CONVERSION OF LOWER ALKANES

[75] Inventors: Philip O. Nubel, Naperville; Larry C. Satek, Wheaton; Michael J. Spangler, Sandwich; Charles A. Lutman, West Chicago; Glenn O. Michaels, South Holland, all of Ill.

[73] Assignee: Amoco Corporation, Chicago, Ill.

[21] Appl. No.: 514,173

[22] Filed: Apr. 25, 1990

[51] Int. Cl.⁵ ............................................... C01C 2/00
[52] U.S. Cl. ........................... 585/500; 585/310; 585/408; 585/641; 585/733; 585/943
[58] Field of Search ............... 570/243; 585/310, 408, 585/500, 641, 733, 943

[56] References Cited

U.S. PATENT DOCUMENTS

| | | | |
|---|---|---|---|
| 4,590,324 | 5/1986 | Satek | 585/444 |
| 4,645,753 | 2/1987 | Zletz et al. | 502/206 |
| 4,714,796 | 12/1987 | Senkan | 585/328 |
| 4,729,979 | 3/1988 | Zletz | 502/206 |
| 4,755,497 | 7/1988 | De Simone et al. | 502/202 |
| 4,769,504 | 9/1988 | Noceti et al. | 585/500 |
| 4,795,843 | 1/1989 | Imai et al. | 585/408 |
| 4,804,797 | 2/1989 | Minet et al. | 585/641 |
| 4,983,783 | 1/1991 | Senkan | 585/943 |

FOREIGN PATENT DOCUMENTS 48,509  9/1985  Soviet Union .

Primary Examiner—Asok Pal
Assistant Examiner—E. D. Irzinski
Attorney, Agent, or Firm—Nick C. Kottis; William H. Magidson; Ralph C. Medhurst

[57] ABSTRACT

A process for the halogen-assisted conversion of lower alkanes to higher molecular weight hydrocarbons is provided. A first reaction mixture including lower alkanes, a hydrogen halide and an oxygen-containing gas are contacted with a catalytic composition of crystalline copper aluminum borate at appropriate reaction conditions to form an intermediate composition including halogenated alkanes. The halogenated alkanes are subsequently contacted with a catalytic composition of a pentasil molecular sieve material under appropriate reaction conditions to form a product mixture including hydrocarbons having molecular weights greater than the lower alkanes.

22 Claims, 1 Drawing Sheet

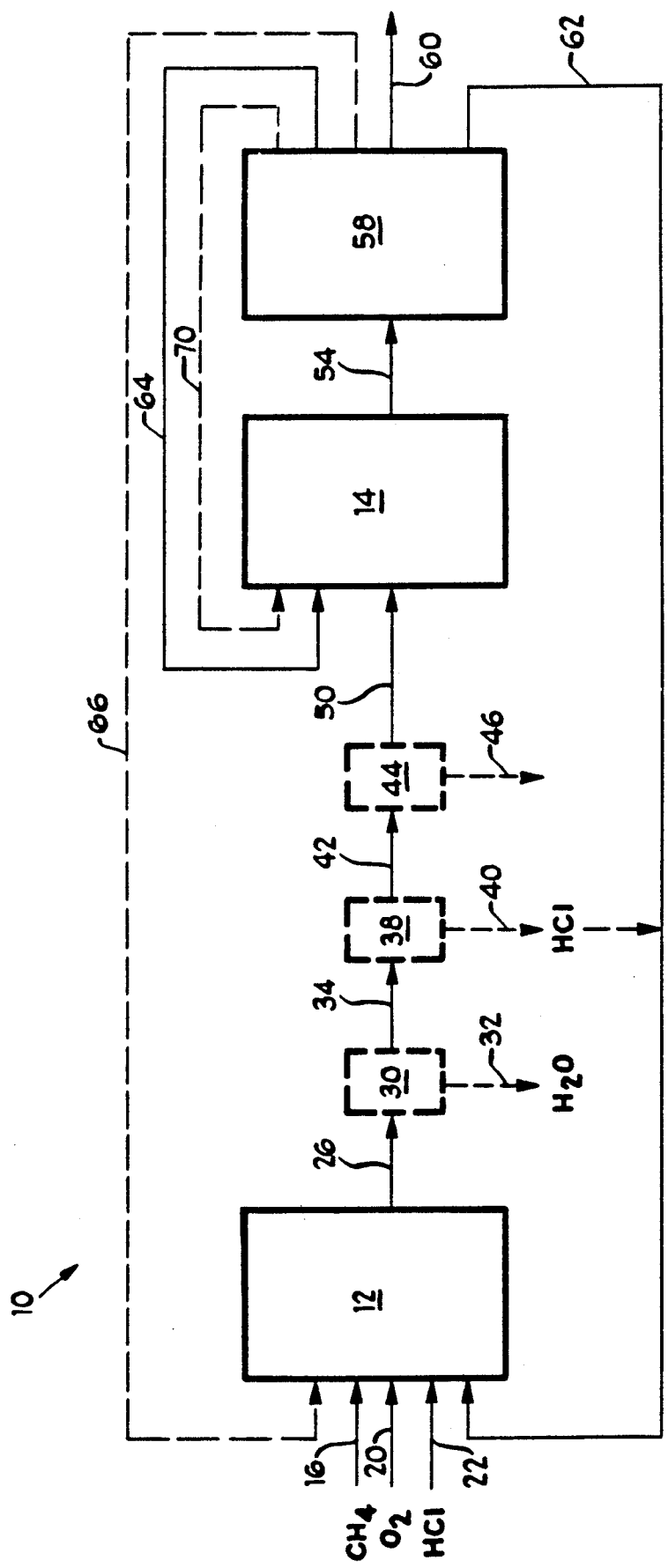

HALOGEN-ASSISTED CONVERSION OF LOWER ALKANES

BACKGROUND OF THE INVENTION

This invention relates generally to the utilization of lower alkanes and the synthesis of hydrocarbons therefrom and, more specifically, to conversion of a low molecular weight alkane, such as methane, to a higher molecular weight hydrocarbon.

As the uncertain nature of ready supplies and access to crude oil has become increasingly apparent, alternative sources of hydrocarbons and fuel have been sought out and explored. The conversion of low molecular weight alkanes (lower alkanes) to higher molecular weight hydrocarbons has received increasing consideration as such low molecular weight alkanes are generally available from readily secured and reliable sources. Natural gas, partially as a result of its comparative abundance, has received a large measure of the attention focused on sources of low molecular weight alkanes. Large deposits of natural gas, mainly composed of methane, are found in many locations throughout the world. In addition, low molecular weight alkanes are generally present in coal deposits and may be formed during numerous mining operations, in various petroleum processes, and in the above- or below-ground gasification or liquefaction of synthetic fuelstocks, such as coal, tar sands, oil shale and biomass, for example. In addition, in the search for petroleum, large amounts of natural gas are discovered in remote areas where there is no local market for its use as a fuel or otherwise. Additional major natural gas resources are prevalent in many remote portions of the world such as remote areas of western Canada, Australia, U.S.S.R. and Asia. Commonly, natural gas from these types of resources is referred to as "remote gas".

Generally, much of the readily accessible natural gas is used in local markets as the natural gas has a high value use as a fuel whether in residential, commercial or industrial applications. Accessibility, however, is a major obstacle to the effective and extensive use of remote gas. In fact, vast quantities of natural gas are often flared, particularly in remote areas from where its transport in gaseous form is practically impossible.

Conversion of natural gas to liquid products is a promising solution to the problem of transporting low molecular weight hydrocarbons from remote areas and constitutes a special challenge to the petrochemical and energy industries. The dominant technology now employed for utilizing remote natural gas involves its conversion to synthesis gas, also commonly referred to as "syngas", a mixture of hydrogen and carbon monoxide, with the syngas subsequently being converted to liquid products. While syngas processing provides a means for converting natural gas to a more easily transportable liquid that in turn can be converted to useful products, the intermediate step involved in such processing, i.e., the formation of the synthesis gas, is typically relatively costly as it involves adding oxygen to the rather inert methane molecule to form a mixture of hydrogen and carbon monoxide. While oxygen addition to the carbon and hydrogen of methane molecules may be advantageous when the desired products are themselves oxygen containing, such as methanol or acetic acid, for example, such oxygen addition is generally undesirable when hydrocarbons such as gasoline or diesel fuel are the desired products as the added oxygen must subsequently be removed. Such addition and removal of oxygen naturally tends to increase the cost associated with such processing.

Methane, the predominant component of natural gas, although difficult to activate, can be reacted with oxygen or oxygen-containing compounds such as water or carbon dioxide to produce synthesis gas. Synthesis gas can be converted to syncrude such as with Fischer-Tropsch technology and then upgraded to transportation fuels using usual refining methods. Alternatively, synthesis gas can be converted to liquid oxygenates which in turn can be converted to more conventional transportation fuels via catalysts such as certain zeolites.

Because synthesis gas processing requires high capital investment, with the syngas being produced in relatively energy intensive ways, such as by steam reforming where fuel is burned to supply heat for reforming, and represents an indirect route to the production of hydrocarbons, the search for alternate means of converting methane directly to higher hydrocarbons continues.

One such alternative method involves methane conversion to higher hydrocarbons via a "chlorine-assisted" route, such as represented by the following 2-step process:

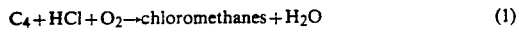

$$C_4 + HCl + O_2 \rightarrow \text{chloromethanes} + H_2O \quad (1)$$

$$\text{chloromethanes} \rightarrow C_{2+} \text{ hydrocarbons} + HCl \quad (2)$$

In the first step of such a process, methane (using HCl and oxygen) is chlorinated to chloromethanes. Such a chlorination step is also referred to as methane "oxychlorination" or "oxyhydrochlorination".

In the second step of such a process, chloromethanes are converted to higher hydrocarbons, e.g., hydrocarbons having 2 or more carbon atoms, represented by "$C_{2+}$", and HCl. The HCl generated in the second step can be recycled back to the first step so that effectively there is no net consumption of chlorine in the overall process.

Such a chlorine-assisted process is not yet practiced commercially.

Catalysts for the chlorination of the hydrocarbons, such as methane, have in the past typically consisted of copper chloride and promoters such as potassium and lanthanum chlorides supported on silica or alumina. For example see *Applied Catalysis*, Vol. 11, pp. 35-71 (1984); *J. Catalysis*, Vol. 99, pp. 12-18 (1986); European Patent Application 0117731, filed Sept. 5, 1984, by British Petroleum; and U.S. Pat. No. 4,123,389 issued Oct. 31, 1978, and assigned to Allied Chemical Corporation.

The role of the potassium and/or lanthanum chloride promoter in such catalysts is not fully understood. It is believed that the presence of such a promoter results in the formation of a supported eutectic mixture of the copper chloride and promoter chloride, which mixture is molten at reaction temperatures. Catalytic activity is believed to be facilitated by the enhanced mass transfer properties of a molten phase relative to a similar composition in a solid phase.

Generally, while such catalysts initially appear relatively active and selective, the use of such catalysts suffers from relatively rapid catalyst deactivation realized during such use of the catalyst. Such deactivation is believed to be due to changes in the active copper species of the catalyst with time as the catalyst is on stream.

In addition, U.S. Pat. Nos. 4,052,468; 4,052,470; 4,060,555; and 4,105,691, all assigned to Allied Chemical Corporation, relate to processes for the production of chlorofluorinated hydrocarbons, such as cycloaliphatic, acyclic, aliphatic ketones and carboxylic acids, respectively, via the use of a Deacon catalyst (such as a metal halide impregnated on a suitable carrier).

The search for a long-lived catalyst effective in catalyzing the halogenation, particularly the chlorination of hydrocarbons, particularly lower hydrocarbons, especially methane, such as could be used in the first step of the above-identified process, has continued.

Catalytically active copper aluminum borate is the subject of commonly assigned Satek U.S. Pat. No. 4,590,324; of commonly assigned Kouba, et al., U.S. Pat. No. 4,613,707; of commonly assigned Zletz, et al., U.S. Pat. No. 4,645,753; of commonly assigned Zletz, U.S. Pat. No. 4,729,979; of commonly assigned De Simone, et al., U.S. Pat. No. 4,755,497; and of commonly assigned copending application Zletz, U.S. Ser. No. 285,103 filed Dec. 14, 1988. These patents and application disclose the preparation, characterization and utility of copper aluminum borate and are hereby incorporated by reference. None of these patents, however, disclose or suggest the use of crystalline copper aluminum borate in a process for the halogenation and, in particular, the chlorination of hydrocarbons.

Further, McArthur, in U.S. Pat. Nos. 3,856,702, 3,856,705 and 4,024,171, discloses that it has been long the practice in the art to impregnate or otherwise distribute active catalytic metals on support materials having desired properties of porosity, surface area, thermal and mechanical stability, and suitably inert chemical properties. McArthur teaches that a superior catalyst support results from calcining certain alumina and boria composites within the temperature range of about 1,250° F.–2,6000° F., which appears to produce a defined crystalline phase of 9 $Al_2O_3 \cdot 2B_2O_3$, following which the aluminum borate support can be impregnated with solution(s) of desired catalytic salt or salts, preferably those that are thermally decomposable to give the corresponding metal oxides. Following impregnation, the finished catalysts are dried and, if desired, calcined at temperatures of 500° to 1000° F., for example. In the final catalyst, the active metal or metals may appear in the free form as oxides or sulfides or in another active form. Examples 1 to 6 of McArthur impregnate the calcined support with an aqueous solution of copper nitrate and cobalt nitrate to provide about 4% copper as CuO and 12% cobalt as $Co_2O_3$ in the final catalyst.

Uhlig, in Diplomarbeit, Institute for Crystallography, Aacken (October 1976) "Phasen—und Mischkristall—Bildung im $B_2O_3$—armeren Teil des Systems $Al_2O_3$—CuO—$B_2O_3$" ("Formation of Phases and Mixed Crystals in that Part of the $Al_2O_3$—CuO—$B_2O_3$ System With a Low $B_2O_3$ Content") which is hereby incorporated by reference, discloses preparation of a green tetragonal solid copper aluminum borate having the structure $Cu_2Al_6B_4O_{17}$ by grinding together solid boron oxide, copper oxide and alumina, sealing the ground metal oxides in a platinum tube and heating same at 1000° C. for a period of 48 hours. Attempts to produce this copper aluminum borate by the indicated route yield well-defined, dense crystalline particles which have an extremely low surface area and are accordingly not suitable for many catalysis processes due to the low porosity and surface area.

Also, Asano, U.S. Pat. No. 3,971,735, discloses a copper-, zinc-, aluminum- and boron-containing catalyst useful in low temperature methanol synthesis. The catalyst is preferably produced by forming a mixture of water-soluble salts of copper, zinc and boron, precipitating same with an alkali carbonate and mixing with alumina. The catalyst is then fired at approximately 300°–450° C.

Relative to the second step of the above-identified process, Brothy, et al., U.S. Pat. No. 4,652,688 and Brothy, et al., U.S. Pat. No. 4,665,270 disclose processes for the conversion of monohalomethanes to hydrocarbons having at least two carbon atoms. In Brothy, et al. '688, the monohalomethane is contacted with a synthetic crystalline gallosilicate zeolite loaded either with at least one modifying cation of hydrogen, metals of Groups I to VIII of the periodic table, or with a compound of at least one Group I to VIII metal. In Brothy, et al. '270, the monohalomethane is contacted with a synthetic crystalline aluminosilicate zeolite having a silica to alumina molar ratio of at least 12:1 and containing cations of either hydrogen, copper or a metal capable of forming an amphoteric oxide, which cations are introduced either by exchange and/or by deposition, provided that when the cation is hydrogen the zeolite is Theta-1.

Butter, et al., U.S. Pat. No. 3,894,017 discloses a process for the conversion of alcohols, mercaptans, sulfides, halides and/or amines to desirable products such as aromatic hydrocarbons as well as other higher molecular weight hydrocarbons. The process utilizes a crystalline aluminosilicate zeolite catalyst having a high silica to alumina ratio of at least about 12 and a constraint index of about 1 to 12. The catalyst also preferably has a crystal density in the hydrogen form of not substantially less than about 1.6.

C. E. Taylor and R. P. Noceti, in a presentation entitled "A Process For Conversion Of Methane To Higher Hydrocarbons" presented at the 6th DOE Indirect Liquefaction Contractors' Conference in Monroeville, Pa., Dec. 3–4, 1986 reported that ZSM-5 is effective for chloromethane conversion to liquid hydrocarbons.

The search for alternative catalysts effective in catalyzing the conversion of halocarbons, in particular, chlorocarbons and especially chloromethanes to liquid hydrocarbons, such as could be used in the second step of the above-identified process, has, however, continued.

Catalytically active, crystalline borosilicate sieve catalyst is the subject of commonly assigned Klotz, U.S. Pat. No. 4,268,420; Klotz, U.S. Pat. No. 4,269,813; Klotz, et al., U.S. Pat. No. 4,285,919 and Published European Application No. 68,796. These patents disclose the preparation, characterization and utility of crystalline borosilicate catalyst and are hereby incorporated by reference.

As described in the references in the paragraph above, catalyst compositions typically are formed by incorporating an AMS-1B crystalline borosilicate molecular sieve material into a matrix such as alumina, silica or silica-alumina to produce a catalyst formulation. In one method of making AMS-1B crystalline borosilicate, sieve material is formed by crystallizing sources for silicon oxide and boron oxide with sodium hydroxide and an organic compound. After crystallization, the resulting sodium form is ion exchanged with an ammonium compound and calcined to yield the hydrogen form of AMS-1B. In another more preferred method, AMS-1B crystalline borosilicate is crystallized in the hydrogen form from a mixture containing a diamine in place of a metal hydroxide. AMS-1B borosilicates in hydrogen form are designated HAMS-1B. Typically, the hydrogen form sieve is gelled with an alumina sol, dried and calcined to yield a catalyst composition.

None of these patents, however, disclose or suggest the use of crystalline borosilicate sieve catalyst in a process for the conversion of halocarbons and, in particular, chlorocarbons to hydrocarbons.

Further, relative to the above-identified process, Noceti, et al., U.S. Pat. No. 4,769,504, discloses a process for the production of aromatic-rich, gasoline boiling range hydrocarbons from lower alkanes, particularly from methane. The process is disclosed as carried out in two stages. In the first, an alkane is reacted with oxygen and hydrogen chloride over an oxyhydrochlorination catalyst such as copper chloride with minor proportions of potassium chloride and rare earth chloride. This produces an intermediate gaseous mixture containing water and chlorinated alkanes. The chlorinated alkanes are subsequently contacted with a crystalline aluminosilicate catalyst in the hydrogen or metal promoted form to produce gasoline range hydrocarbons with a high proportion of aromatics and a small percentage of light hydrocarbons ($C_2$–$C_4$). The light hydrocarbons can be recycled for further processing over the oxyhydrochlorination catalyst.

Imai, et al., U.S. Pat. No. 4,795,843 disclose treating methane with a haliding agent, such as chlorine, bromine or iodine to form a methyl halide which subsequently may be converted into usable products by contacting the halides with a conversion catalyst of silicalite, a particular type of crystalline silica material. Such a catalyst is disclosed as being less active than a crystalline aluminosilicate having a silica to alumina ratio of about 20:1 but has improved stability relative to such a crystalline aluminosilicate.

SUMMARY OF THE INVENTION

It is an object of the present invention to overcome one or more of the problems described above.

According to the invention, a method for converting lower alkanes to higher molecular weight hydrocarbons is provided wherein a first reaction mixture including lower alkanes, a hydrogen halide and an oxygen-containing gas are contacted with a catalytic composition of crystalline copper aluminum borate at appropriate reaction conditions to form an intermediate composition including halogenated alkanes. The halogenated alkanes are subsequently contacted with a catalytic composition of a pentasil molecular sieve material under appropriate reaction conditions to form a product mixture including hydrocarbons having molecular weights greater than the lower alkanes.

In one embodiment of the invention, a method for converting methane to higher molecular weight hydrocarbons which includes the steps of contacting a first reaction mixture including methane, HCl and an oxygen-containing gas with a first catalyst of crystalline copper aluminum borate, having a specified X-ray diffraction pattern, under appropriate reaction conditions to form an intermediate composition including chloromethane. Followed by contacting the chloromethane with a second catalytic composition including crystalline borosilicate and a porous refractory inorganic oxide to form hydrocarbon products having molecular weights greater than the methane. In such a second catalytic composition, the borosilicate and inorganic oxide have been intimately admixed with one another and the borosilicate includes a molecular sieve material having a specified composition in terms of mole ratios of oxides and also a specified X-ray diffraction pattern.

In another embodiment of the invention which provides a method for converting methane to higher molecular weight hydrocarbons, a reaction mixture comprising methane, HCl, and an oxygen-containing gas is contacted with a catalyst of crystalline copper aluminum borate and a promoting amount of alkali metal compound, under appropriate reaction conditions, to form an intermediate composition comprising chloromethane, wherein the chloromethane includes methyl chloride. The crystalline copper aluminum borate has a specified X-ray diffraction pattern and a surface area in the range of about 0.1 to about 300 $m^2/g$. The methyl chloride is then contacted with a second catalytic composition comprising crystalline borosilicate, a porous refractory inorganic oxide and a promoter material of at least one of iron and gallium to form a product stream comprising hydrocarbons having a higher molecular weight than methane. The borosilicate and inorganic oxide of the second catalytic composition having been intimately admixed with one another with the borosilicate comprising a molecular sieve material having a specified composition in terms of mole ratios of oxides and also a specified X-ray diffraction pattern.

Other objects and advantages of the invention will be apparent to those skilled in the art from the following detailed description taken in conjunction with the appended claims.

BRIEF DESCRIPTION OF THE DRAWING

The FIGURE is a simplified schematic flow diagram of a system for the conversion of methane to higher molecular weight hydrocarbons in accordance with one preferred embodiment of the invention.

DETAILED DESCRIPTION OF THE INVENTION

The present invention provides a method for converting lower alkanes to higher molecular weight hydrocarbons.

While the process of the invention is described hereinafter with particular reference to the conversion of methane, it will be apparent that the process also has application in the conversion of natural gas and other lower hydrocarbons, particularly paraffinic lower hydrocarbons such as ethane and propane, and combinations of ethane and/or propane with or without methane, for example. It is to be understood, however, that while the method may also be utilized with higher hydrocarbon feedstocks, particularly higher alkane feedstocks, such use may, as result of competing reaction kinetics, result in a reduction in the amount of higher molecular weight hydrocarbons formed thereby. It is to be further understood, however, that at the present time the invention is perceived to have particular utility in the conversion of lower alkanes (i.e., $C_1$–$C_4$ alkanes), and especially methane.

Also, while the process of the invention is described hereinafter with particular reference to a chlorine-assisted route of conversion, the invention is believed to also have applicability to the use of other halogens, such as fluorine, iodine and, in particular, bromine to assist in the conversion. For example, hydrogen bromide could be used in the process to form brominated alkanes which in turn could be reacted to form hydrocarbons having molecular weights greater than the original lower alkanes.

Referring to the FIGURE, a simplified schematic flow diagram of a system for the conversion of methane to higher molecular weight hydrocarbons and generally designated by the numeral 10 is shown. The system 10 includes a first reactor 12 wherein, as described below, methane is chlorinated and a second reactor 14 wherein, as described below, chlorinated methane product is subsequently converted to higher hydrocarbons.

In the system 10, a stream 16 of methane is fed to the reactor 12. In addition, a stream 20 of an oxygen-containing gas, e.g., pure oxygen, and a stream 22 of HCl are also fed to the reactor 12. It is to be understood, however, that other oxygen-containing gases such as air or oxygen-enriched air, for example, may be used as the oxygen-containing gas or as a supplement to pure oxygen.

In the reactor 12, methane, HCl, and oxygen are contacted with a catalyst of crystalline copper aluminum borate, as will be described below, at appropriate reaction conditions to form chloromethane products.

A stream 26, typically containing chloromethane products and water as well as unreacted methane, unreacted HCl, unreacted oxygen, other chlorocarbon products and, if an oxygen-containing gas such as air was used, inert materials such as nitrogen, is passed from the reactor 12. If desired, $H_2O$ can be substantially removed from the stream 26 via a separator 30 to form a $H_2O$ stream 32 and a stream 34 substantially free of $H_2O$. Such water separation and removal can be effected through common or known water separation techniques such as through the use of a scrubber column packed with an absorbant material such as a molecular sieve having a high affinity for water.

The HCl contained in the stream 34 can, if desired, also be separated therefrom via a separator 38 to form a stream 40 of HCl and a stream 42 substantially free of HCl. Such separation can be effected, for example, in an aqueous scrubber wherein the HCl would dissolve in water. The acidic water can then be recovered and dried with the recovered HCl being recycled to the reactor 12.

If desired, the steam 42 can be treated in a separator 44 to separate therefrom chlorocarbons other than methyl chloride as a stream 46. In so doing a stream 50 substantially free of chlorocarbons other than methyl chloride is formed. For example, such chlorocarbon removal can be effected by means of a distillation column with the chlorocarbons so separated, if desired, being subjected to further treatment such as combustion/oxidation to yield HCl and carbon oxides, which HCl can be recovered and used in the earlier portion of the subject process, for example.

The stream 50 is passed to the second reactor 14 wherein methyl chloride is converted to hydrocarbons having a higher molecular weight than methane. In the reactor 14 the methyl chloride is contacted with a catalyst which includes a pentasil molecular sieve material such as a crystalline aluminosilicate (e.g., ZSM-5), silicalite, or, preferably, a crystalline borosilicate, as will be described below, at appropriate reaction conditions to form hydrocarbons, such as chain hydrocarbons of three or more carbon atoms and aromatics, for example, which hydrocarbons have a higher molecular weight than methane. An effluent stream 54 from the reactor 14 is passed to a separator means 58, such as a distillation column, whereby desired separation of the effluent stream contents is effected. Resulting from the separator means 58 will be a product stream 60 containing the higher molecular weight hydrocarbons formed in the process. Also, a stream 62 containing HCl, such as resulting from the reactions occurring in reactor 14, as will be described below, is formed, and preferably is recycled to the reactor 12. In addition, if desired, HCl separated from the effluent stream of the reactor 12, e.g. the stream 40, can be combined with the stream 62 for recycle to the reactor 12.

A stream 64 containing methyl chloride which passed through the reactor 14 unreacted is preferably recycled to the reactor 14 for additional processing. A stream 66 containing paraffins and olefins may, if desired, be fed to the reactor 12 for further processing.

Alternatively, or in addition, if desired, a stream 70 containing olefins can be recycled to the reactor 14 for further processing.

In the chlorination of methane in accordance with the invention, a first reaction mixture including methane, HCl and an oxygen-containing gas, such as pure oxygen, air, or oxygen-enriched air, for example, is contacted with a catalyst of crystalline copper aluminum borate at appropriate reaction conditions to form chloromethane products such as methyl chloride, dichloromethane, chloroform, carbon tetrachloride, or various mixtures of these.

Such catalytic chlorination of methane can be performed at reaction temperatures of about 100° C. to about 700° C., preferably at reaction temperatures of about 250° C. to about 500° C. In addition, the pressure at which the process is effected is not, within reasonable bounds such as operation at from about 10 psia to about 2000 psia, believed critical and may be selected in view of overall processing economics and schemes. Also, while the process will be described hereinafter with reference to general operation in a continuous mode operation with a Gas Hourly Space Velocity (GHSV), defined as the volume of reactant gas at STP per volume of catalyst per hour, for continuous operation suitably being in the range from about 1 to about 10,000 volume per volume per hour and a reactant-catalyst contact time being in the range of about 0.1 second to about 100 seconds, it is to be understood that the process can be performed in a batch-type mode of operation, if desired.

As described above, the oxygen-containing gas as used in the practice of the invention can be pure oxygen, air, or oxygen-enriched air, for example. Thus, the oxygen-containing gas can contain diluents such as the inert gases, nitrogen, helium, argon, etc., as well as diluents, such as carbon dioxide, which are generally inert under the subject reaction conditions. The oxygen-containing gas will, however, preferably contain at least 1 volume percent oxygen.

Further, the components of this first reaction mixture, i.e., methane, HCl, and an oxygen-containing gas, can be employed in any desired effective ratio. Suitable ratios of C:Cl:O are best determined experimentally. Typically, the ratio of carbon atoms to chlorine atoms to oxygen atoms will be in the range of about 10:0.1–100:0.1–100 and preferably 10:1–50:1–50, with the selection of an appropriate operating ratio typically influenced by factors such as desired methane conversion, desired chlorocarbon product, etc. For example, in the chlorination of methane, if conversion of relatively greater amounts of methane are desired, then relatively greater amounts of HCl and oxygen may preferably be employed. Further, if a high reaction selectivity to monochloromethane products, as opposed to higher chlorinated methane products, e.g., dichloromethane, trichloromethane, and tetrachloromethane, is desired then relatively lower amounts of HCl and oxygen may preferably be employed. Also, use of methane in relative amounts in excess of the stoichiometric amounts required for the formation of the desired chlorocarbon product generally results in the production of relatively smaller, or minor, amounts of carbon oxides ($CO_x$), i.e., CO and $CO_2$. Reduction in carbon oxide production is generally preferred when seeking to minimize carbon atom loss to undesired products (e.g., in chlorocarbon formation in which carbon oxide formation is undesired, it will generally be preferred to employ methane in a relative amount in excess of the stoichiometric amount required in the desired chlorocarbon).

In addition, this first reaction mixture may also contain other components such as other hydrocarbons, oxygenated hydrocarbons (e.g., alcohols, ketones, etc.), halocarbons, water, chlorine ($Cl_2$), carbon oxides (CO and/or $CO_2$), and inert gases such as nitrogen, helium, argon, etc.

The catalysts employed in the practice of this portion of the invention are crystalline copper aluminum borates, e.g., crystalline copper-aluminum-boron mixed oxide materials, such as described in the previously identified patents and patent application.

Neat copper aluminum borate having the empirical formula $Cu_2Al_6B_4O_{17}$ is a crystalline compound, green in color. For catalytic studies, neat copper aluminum borate is generally prepared as a microcrystalline material. The crystal structure of the material has been determined by neutron and X-ray powder diffraction methods as well as by single crystal X-ray diffraction to obtain a precise description of the structure. Neat copper aluminum borate crystallizes in the tetragonal space group I4/m with a=10.5736(7) Angstroms and c=5.6703(6) Angstroms. The structure contains edge sharing chains of octahedral Al atoms parallel to the c-axis. These planes are joined in the a-axis and b-axis directions by trigonal planar $BO_3$ groups. The unit cell contains trigonal bipyramidal sites, randomly equally occupied by either Cu or Al atoms, which share a face with the Al atom octahedron. These trigonal bipyramidal sites share equatorial corners at a square planar O atom. The structure also contains 8 ring channels parallel to the c-axis and approximately 4 Angstroms in diameter.

The catalysts for use in the practice of the present invention may be prepared by various methods including the solid-state preparation technique described in DeSimone, et al., U.S. Pat. No. 4,755,497, issued July 5, 1988, the disclosure of which is hereby incorporated herein by reference, but preferably is prepared by the technique described in the pending application, Satek, U.S. Ser. No. 361,278, filed June 5, 1989, the disclosure of which is hereby incorporated by reference.

In such a process for producing copper aluminum borate, a homogeneous gel is formed of an aqueous-organic medium comprising a volatile organic liquid having at least partial miscibility with water. Useful volatile organic compounds will typically have normal boiling points in a temperature range downward from about 140° C. Suitable organic compounds include alcohols, ethers, aldehydes and ketones having from about 1 to about 5 carbon atoms per molecule, such as methanol, ethanol, 2-propanol, 2-butanol, 2-methyl-2-propanol, 2-propen-1-ol, methoxymethane, methoxyethane, 1-methoxypropane, 2-methoxypropane, 2-ethoxypropane, 1,3-dioxane, 1,4-dioxane, propanone, butanone, 3-pentanone, and 2-pentanone, and N,N-dimethylformamide. Of these organic compounds, methanol, ethanol, and N,N-dimethylformamide are preferred.

Advantageously, the amounts of water and volatile organic liquid used are the least amounts needed to consistently obtain a homogeneous copper aluminum borate precursor. Likewise, suitable ratios of organic liquid to water for each liquid system are best determined experimentally. Typically, the ratios of organic liquid to water by volume are less than about 1, preferably in a range from about 0.01 to about 0.99, more preferably in a range from about 0.1 to about 0.9.

More specifically, the method for producing a copper aluminum borate precursor comprises forming an aqueous composition comprising a source of copper(II) ions, a source of alumina, and a source of boria, admixing with the aqueous composition a volatile organic liquid containing a chemical base to form a homogeneous gel which, when dried to form a superficially dry solid and/or calcined to a sufficiently high temperature, forms crystalline copper aluminum borate.

A sol or any reasonably soluble salt of copper(II) ions or precursor thereof, which is at least partially soluble in the dispersing liquid, such as the acetate, formate, nitrate, carbonate, chloride, and the like, can be a suitable source of copper for use in this catalytic composition. Salts of copper(II) such as copper(II) nitrate, copper(II) acetate, copper(II) carbonate, etc. are preferred. Copper(II) nitrate is preferred as it behaves well in air drying. When the source of copper(II) is a sol, oxides are preferred.

Typically, best results are obtained when each of the sources used is chosen to reduce the content of foreign anions and cations in the reaction mix.

The source of alumina can be any material capable of producing alumina, such as aluminum nitrate, aluminum acetate, aluminum borate, etc. It is preferred, however, that the source of alumina be a well-dispersed liquid, such as an alumina sol.

The source of boria is a material such as borate or boric acid with pure boric acid being preferred.

Generally, these components can be combined in an aqueous or aqueous-organic medium in approximately stoichiometric proportions sufficient to provide copper aluminum borate having the mixed metal oxide formula $2CuO \cdot 3Al_2O_3 \cdot 2B_2O_3$ or the empirical formula $Cu_2Al_6B_4O_{17}$.

Typically, the mole ratios of the various reactants can be varied to produce the copper aluminum borate by this method. Specifically, the mole ratios in terms of oxides of the initial reactant concentrations are characterized by the general mixed oxide formula $$(x)CuO \cdot (y)Al_2O_3 \cdot (z)B_2O_3$$

wherein x, y and z are numbers representing molar amounts of the oxides of the source reagents.

The mole ratios of $CuO/B_2O_3$, calculated as x/z, are about 0.1 to about 20, preferably about 0.15 to about 10, and most preferably about 0.25 to about 6, and the mole ratios of $Al_2O_3/B_2O_3$, calculated as y/z, are from about 0.1 to about 20, preferably about 0.15 to about 10, and more preferably about 0.25 to about 6.

In somewhat greater detail, a preferred preparation procedure is to dissolve the boria source and disperse the alumina source in water or a volatile organic liquid and water by mixing in a blender for about 3-5 minutes and then adding an aqueous sol or solution of a source of copper(II) to the blender followed by gelation by admixing with the aqueous mixture a volatile, organic liquid, preferably methanol, ethanol, or N,N-dimethylformamide, containing a basic chemical compound.

Suitable basic compounds include oxides, hydroxides and salts of alkali metal elements, ammonium hydroxide, and hydroxides of organic cations, such as methylammonium hydroxide or tetramethylammonium hydroxide. Preferred basic chemical compounds comprise at least one quaternary ammonium cation selected from the group consisting of tetramethylammonium, tetraethylammonium, benzyltrimethylammonium, trimethyl-n-octylammonium, dibenzyldimethylammonium, and cetyltrimethylammonium. The presence of the ammonia as well as other volatile components in the gelled mixture, such as acetate ion, nitrate ion, etc., is advantageous in providing the final calcined solid with sufficiently high surface area and porosity desirable for catalytic reactions.

Typically, the pH of the aqueous mixture is in a range from about 4 to about 12. If the reaction media is too acidic or too basic, the desired solid generally will not form, or other contaminating phases are formed in addition to the desired product. To some extent the pH of the reaction mixture controls surface properties of the final calcined solid material. Preferably, the pH of the reaction mixture is in a range from about 5 to about 9, more preferably about 5.5 to about 8, in order to gel the reaction mixture.

The gelled mixture is mildly dried, such as for a period of time ranging from a few hours to a few days at varying temperatures, typically about 20° to about 225° C., to form a dry cake which is a copper aluminum borate precursor. Advantageously, the gelled mixture is allowed to air-dry, usually for about 1-3 days, followed by vacuum drying, typically at a pressure of about 0.3 atmosphere for about 15 to 25 hours at about 100° C. to 150° C. with a purge of dry gas, such as nitrogen.

The superficially dry precursor is calcined, preferably at a temperature within the range of about 650° to about 1000° C. for a reaction time that is sufficient to effect formation of crystalline copper aluminum borate, typically a reaction time within the range of about 2 to about 3 hours. Samples of material can be removed during calcination to check the degree of crystallization and determine the optimum calcination time.

The crystalline material formed can be crushed to a powder or to small particles and extruded, pelletized, or made into other forms suitable for its intended use. In a preferred embodiment of the above-described method, the crystalline material formed can be washed with a solvent, preferably an aqueous solvent, which removes impurities such as excess boria, without destroying the crystalline material formed, mildly dried for anywhere from a few hours to a few days at varying temperatures, typically about 50° to about 225° C., to form a dry cake which can then be treated as required for its intended use.

The dry, copper aluminum borate catalyst precursor is subsequently calcined, which calcination is usually carried out at a temperature in the range of from about 650° C. to about 900° C. and preferably at a temperature of about 700° C. to about 850° C. for about 0.1 hour to about 24 hours, and typically in air. In practice, higher calcination temperatures are typically associated with shorter calcination times.

These solid catalyst materials can be admixed with or incorporated within various binders or matrix materials if desired. They can be combined with active or inactive materials, synthetic or naturally occurring oxides, as well as inorganic or organic materials which would be useful for binding such substances. Well-known materials include silica, silica-alumina, alumina, magnesia, titania, zirconia, alumina sols, hydrated aluminas, clays such as bentonite or kaolin, Sterotex (a powdered vegetable stearine produced by Capital City Products, Co., Columbus, Ohio), or other binders well known in the art.

The X-ray diffraction patterns in Table I show the significant lines for unreduced CuAB of this invention and CuAB of Uhlig.

X-ray data were determined by standard techniques. The radiation was the K-alpha doublet of copper, and a proportional counter spectrometer with a strip chart pen recorder was used. The peak heights, I, and the positions as a function of 2 times theta, where theta is the Bragg angle, were read from the spectrometer chart. From these the relative intensities, 100 $I/I_0$, where $I_0$ is the intensity of the strongest line or peak, and d (obs.), the interplanar spacing in Angstroms, corresponding to the recorded lines, were calculated. In Table I, the relative intensities are given in terms of the symbols VVS=very very strong (>100), VS=very strong (80-100), S=strong (50-80), M=Medium (20-50), W=weak (10-20) and VW=very weak (<10).

TABLE I

| (d)Angstroms | CuAB | Uhlig CuAB |
|---|---|---|
| 7.50 ± .1 | VM-M | M |
| 5.29 ± .05 | VS | VS |
| 5.00 ± .05 | S | S |
| 4.92 ± .03 | | |
| 3.73 ± .03 | W-M | W |
| 3.64 ± .03 | VW-W | VW |
| 3.58 ± .03 | | |
| 3.35 ± .03 | W | W |
| 2.98 ± .03 | VW-W | W |
| 2.84 ± .03 | VW-W | VW |
| 2.78 ± .02 | | |
| 2.64 ± .02 | M-S | M |
| 2.61 ± .02 | W-M | W |
| 2.50 ± .02 | W-M | VW |
| 2.45 ± .02 | | |
| 2.26 ± .02 | W-M | W |
| 2.22 ± .02 | | |
| 2.16 ± .02 | M | W |
| 2.13 ± .02 | | |
| 2.07 ± .02 | M | M |
| 1.97 ± .02 | M | W-M |
| 1.91 ± .02 | | VW |
| 1.86 ± .01 | W-M | VW |
| 1.81 ± .01 | M | W |
| 1.76 ± .01 | VW | VW |
| 1.67 ± .01 | W-M | W |
| 1.60 ± .01 | W-VW | VW |
| 1.555 ± .01 | W-VW | VW |

The significant X-ray diffraction lines for copper aluminum borate are set forth below in Table A, with the symbols, e.g., VS, S, M, W, etc., for relative intensities corresponding to the previously indicated ranges.

TABLE A

| (d)Angstroms | Strength |
| --- | --- |
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M |

It has been found that the addition of a promoting amount of an alkali metal-containing compound to such crystalline copper aluminum borates results in a catalyst having improved selectivity performance, i.e., reduction in yield by undesired carbon oxide byproducts, e.g., CO and $CO_2$. For example, the incorporation of compounds such as chlorides, oxides, for example, of alkali metals such as potassium or lithium, for example, into the copper aluminum borate catalyst results in a catalyst which yields lesser amounts of carbon oxides at equivalent conversion levels than do similar, unmodified copper aluminum borate catalysts. This effect is surprising since the copper aluminum borate materials are crystalline and not likely to form eutectic melts as do conventional copper chloride catalysts as described above. Also, in contrast to the above-described chlorination catalysts of copper chloride and promoters such as potassium and lanthanum chlorides supported on silica or alumina, compounds of other alkali metals, such as lithium, as well as alkali metals (including potassium) in nonchloride compounds, such as in the form of oxides, have proven effective in promoting catalyst selectivity. In addition, the incorporation of compounds such as hydroxides, carbonates, nitrates, bromides, iodides, sulfates, acetates, etc. of such alkali metals into the copper aluminum borate catalyst is also believed to similarly result in a catalyst which yields lesser amounts of carbon oxides at equivalent conversion levels than do similar, unmodified copper aluminum borate catalysts.

Further, the X-ray diffraction powder patterns of the used and new catalysts are nearly identical for all cases, including the potassium chloride- and potassium oxide-doped materials. This indicates, in contrast to other processes using such copper aluminum borate catalysts, that this process does not involve substantial catalyst degradation to copper metal on a matrix, currently believed to be an aluminum borate with copper ions incorporated as if in a solid solution. The used catalysts, including the potassium chloride- and potassium oxide-doped materials do, however, exhibit some incorporation of chlorine. This incorporated chlorine is dispersed throughout the catalyst particle and may be incorporated into the crystal lattice.

Such catalysis, in contrast to other catalytic processes involving the use of such copper aluminum borate, does not involve substantial catalyst degradation to copper on alumina borate.

Incorporation of the potassium compound may be performed during the catalyst preparation or afterwards by impregnation of the finished crystalline copper aluminum borate. Impregnation may be accomplished by any suitable technique, such as aqueous incipient wetness impregnation, for example. Further, if potassium oxide is desired as the modifier/promoter, impregnation with potassium carbonate or nitrate is preferred, followed by high temperature calcination to yield the supportive oxide. Other potassium compounds, including potassium acetate, hydroxide, sulfate, and chloride, are suitable for use for impregnation. Generally, the promoter-including crystalline copper aluminum borate will contain about 0.1 to about 50 weight percent of the alkali metal-containing compound and preferably will contain about 1 to about 30 weight percent of the alkali metal-containing compound.

In the conversion of methyl chloride to hydrocarbons having a higher molecular weight than methane, the methyl chloride is contacted with a catalyst which includes a pentasil molecular sieve material at appropriate reaction conditions to form hydrocarbons having a higher molecular weight than methane, such as chain hydrocarbons of 3 or more carbon atoms and aromatics, for example.

Such catalytic chloromethane conversion can be performed at reaction temperatures of about 100° C. to about 600° C., preferably about 250° C. to about 450° C. In addition, the pressure which the process is effected is not, within reasonable bounds such as operation at from about 1 psig to about 10,000 psig (preferably from about 10 psig to about 1000 psig), believed critical and may be selected in view of overall processing economics and schemes. Also, while the process will be described hereinafter with reference to operation in a continuous mode-type operation, it is to be understood that the process can be performed in a batch mode, if desired. In operation, the Weight Hourly Space Velocity (WHSV) defined as the weight of reactant feed per weight of catalyst per hour, is suitably in the range of about 0.1 to about 100 gram per gram per hour and the reactant-catalyst contact time is suitably in the range of about 0.1 second to about 100 seconds.

Also, the reaction mixture may, if desired, contain other components such as other hydrocarbons (such as $C_2$-$C_4$ hydrocarbons), oxygenated hydrocarbons (such as alcohols, ethers, etc.), inert gases (such as nitrogen, helium, etc.), carbon oxides (i.e., CO, $CO_2$), water, HCl, and other halocarbons.

The pentasil molecular sieve material used in the catalyst composition includes materials such as crystalline aluminosilicate (e.g., ZSM-5), silicalite, or preferably, a crystalline borosilicate.

The catalyst compositions utilizing a crystalline borosilicate as the pentasil molecular sieve material are based on AMS-1B crystalline borosilicate molecular sieve, which is described in U.S. Pat. Nos. 4,268,420, 4,269,813, and 4,285,919 and Published European Patent Application 68,796, all incorporated herein by reference. AMS-1B crystalline borosilicate generally can be characterized by the X-ray pattern listed in Table II and by the composition formula:

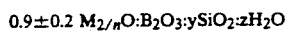

$$0.9 \pm 0.2 \; M_{2/n}O:B_2O_3:ySiO_2:zH_2O$$

wherein M is at least one cation having a valence n, y is between 4 and about 600 and z is between 0 and about 160.

TABLE II

| d-Spacing Å (1) | Assigned Strength (2) |
| --- | --- |
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |

TABLE II-continued

| d-Spacing Å (1) | Assigned Strength (2) |
|---|---|
| 3.62 ± 0.05 | M-MS |
| 2.97 ± 0.02 | W-M |
| 1.99 ± 0.02 | VW-M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mol ratios of the various reactants can be varied to produce the crystalline borosilicates of this invention. Specifically, the mol ratios of the initial reactant concentrations are indicated below:

|  | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^{-2}$ | 10–4000 | 10–500 | 10–500 | wherein R is an organic compound and M is at least one cation having the oxidation state n, such as an alkali or an alkaline earth metal cation or hydrogen. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a base, a boron oxide source, and an organic template compound in water (preferably distilled or deionized water). The order of addition usually is not critical, although a typical procedure is to dissolve base and boric acid in water and then add the template compound. Generally, the silicon oxide compound is added with intensive mixing such as that performed in a Waring Blendor and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of materials affording silicon oxide useful in this invention include silicic acid, sodium silicate, tetraalkyl silicates and Ludox, a stabilized polymer of silicic acid manufactured by E. I. DuPont de Nemours & Co. Typically, the oxide of boron source is boric acid although equivalent species can be used such as sodium borate and other boron-containing compounds.

Cations useful in formation of AMS-1B crystalline borosilicate include alkali metal and alkaline earth metal cations such as sodium, potassium, lithium, calcium, and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, form by replacing such metal cation hydroxides with an organic base such as ethylenediamine as described in Published European Application 68,796.

Organic templates useful in preparing AMS-1B crystalline borosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0±0.2 using a compatible acid or base such as sodium bisulfate or sodium hydroxide. After sufficient quantities of a silica source such as a silicic acid polymer (Ludox) are added with intensive mixing, preferably the pH is again checked and adjusted to a range of about 11.0±0.2.

Alternatively, AMS-1B crystalline borosilicate molecular sieve can be prepared by crystallizing a mixture of sources for an oxide of silicon, an oxide of boron, an alkyl ammonium compound and ethylenediamine such that the initial reactant molar ratios of water to silica range from about 5 to about 25, preferably about 5 to about 20 and most preferably from about 10 to about 15. In addition, preferable molar ratios for initial reactant silica to oxide of boron range from about 4 to about 150, more preferably from about 5 to about 80 and most preferably from about 5 to about 20. The molar ratio of ethylenediamine to silicon oxide should be about above about 0.05, typically below 5, preferably between about 0.1 and about 1.0 and most preferably between about 0.2 and 0.5. The molar ratio of alkylammonium compound, such as tetra-n-propylammonium bromide, to silicon oxide can range from 0 to about 1 or above, typically above about 0.005, preferably about 0.01 to about 0.1, more preferably about 0.01 to about 0.08 and, most preferably, about 0.02 to about 0.05.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization determine the optimum crystallization time.

The crystalline material formed can be separated and recovered by well-known means such as filtration with aqueous washing. This material can be mildly dried for anywhere from a few hours to a few days at varying temperatures, typically about 50°–225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° C. to about 850° C. and preferably about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure, either before or after incorporation into a matrix, by ion exchange, impregnation, a combination thereof, or other suitable contact means. Before placing a catalytically active metal ion or compound on the borosilicate structure, the borosilicate should be in the hydrogen form. If the sieve was prepared using a metal hydroxide, such as sodium hydroxide, the hydrogen form typically is produced by exchange one or more times with ammonium ion, typically using ammonium acetate, followed by drying and calcination as described above.

The original cation in the AMS-1B crystalline borosilicate can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for chlorocarbon conversion.

For example, ions of gallium and iron have proven to be preferred replacement cations for incorporation in catalytic compositions effective for the conversion of chloromethanes to higher molecular weight hydrocarbons, such as described above. Thus, the catalytic compositions of the invention may preferably contain a promoter material of at least one element selected from the group of iron and gallium, for example, as the addition of such promoter materials enhance the conversion of methyl chloride over the catalytic composition as compared to the conversion over similar compositions in the absence of such promoter materials. It being understood that by the term "promoter material," what is meant is the incorporation of the designated element in the catalyst composition in a form, such as cations of gallium or iron, for example, which results in the composition having greater catalytic activity, especially for chlorocarbon conversion, as compared to the similar composition but not containing the promoter material.

Ion exchange and impregnation techniques are well-known in the art. Typically, an aqueous solution of a cationic species is exchanged one or more times at about 25° C. to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about 30 weight percent, typically from about 0.05 to about 25 weight percent, depending on the process use intended. (Where weight percents are in reference to the final catalyst, e.g., the borosilicate with the active material placed thereon.) The optimum amount can be determined easily by routine experimentation.

The hydrogen form of the borosilicate is typically produced by an exchange one or more times with ammonium ions, typically using ammonium acetate followed by drying and calcination as described above. The borosilicate is converted into the hydrogen form by the calcination. Alternatively, the hydrogen form of the borosilicate which is directly produced by the process according to Published European Application No. 68,796 can be used in the process of this invention. The hydrogen form of the borosilicate catalyst will be called HAMS-1B hereinafter.

The AMS-1B crystalline borosilicate useful in this invention is preferably admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material, e.g., the inorganic oxide, can be physically admixed. Typically, such borosilicate compositions can be pelletized or extruded into useful shapes. The crystalline borosilicate content can vary anywhere from a few up to 100 wt. % of the total composition. Catalytic compositions crystalline borosilicate material and preferably contain about 10 wt. % to about 95 wt. % of such material and most preferably contain about 20 wt. % to about 80 wt. % of such material.

The following examples simulate various aspects involved in the practice of the invention. It is to be understood that all changes and modifications that come within the spirit of the invention are desired to be protected and thus the invention is not to be construed as limited by these examples.

EXAMPLES

Example 1

A crystalline copper aluminum borate catalyst, prepared by the solid-state preparation technique of De Simone, et al., U.S. Pat. No. 4,755,497, containing a crystalline copper aluminum borate phase with a 2:3:2 $CuO:Al_2O_3:B_2O_3$ composition and, by ICP elemental analysis containing 23.3 wt. % copper, 26.6 wt. % aluminum, and 8.6 wt. % boron; and having a BET (Digisorb) surface area of 26 $m^2/g$ in ⅛ inch pellet form was ground and sieved to 20-35 mesh prior to testing for methane chlorination.

Catalyst testing was performed using a fixed-bed, single-pass quartz tube flow reactor unit. The reactor was a 18 in long, 16 mm OD quartz tube with a 4 mm OD quartz center thermowell and was operated in downflow mode. Heat was supplied by a 12 in long, three-zone tube furnace. Catalyst beds were supported with alpha-alumina (30–50 mesh) and quartz wool packing materials. A catalyst charge of 5.0 g, corresponding to a 3 in bed length, was centered in the heated portion of the reactor. A pre-blended gas feed mixture consisting of 10 mol % methane, 5 mol % oxygen, 10 mol % HCl, and 75 mol % nitrogen (prepared by Matheson) was employed; feed mixture flow was controlled by a mass flow controller. All runs were performed at 1 atm reactor pressure. Reactor effluent gas and feed gas samples were analyzed by gas chromatography using a TC detector. The nitrogen in the feed mixture was employed as an internal GC standard in order to calculate conversions and selectivities.

Table III presents the results of methane chlorination runs with this crystalline copper aluminum borate catalyst.

as used in Example 1 was used. A feed flow rate of 60 mL/min (0.094 WHSV methane) was used.

Discussion

At the initiation of the run, methane conversion was about 36% and oxygen conversion was about 69%. By the end of the 19 hr run, methane conversion had decreased to 31% and oxygen conversion had declined to 58%. The small declines in methane and oxygen conversion over the 19 hr run period, indicated a relatively low rate of onstream catalyst deactivation.

Example 4

A crystalline copper aluminum borate catalyst containing: a crystalline copper aluminum borate phase with a 2:3:2 $CuO:Al_2O_3:B_2O_3$ composition, an ICP Elemental Analysis of 21.6 wt. % copper, 28.1 wt. % aluminum, and 7.4 wt. % boron; and a BET (Digisorb) surface area of 131 $m^2/g$, prepared by the sol/gel technique described above, was prepared whereby the ma-

TABLE III

| Run Temp (°C.) | Feed Rate (mL/min @ RT & 1 atm) | $CH_4$ WHSV (1/hr) | $CH_4$ Conv. | $O_2$ Conv. | Mole % Selectivities for Carbon-Containing Products | | | | | |
|---|---|---|---|---|---|---|---|---|---|---|
| | | | | | $CH_3Cl$ | $CH_2Cl$ | $CHCl_3$ | $CCl_4$ | CO | $CO_2$ |
| 350 | 90 | 0.071 | 10.7 | 7.1 | 100 | 0 | 0 | 0 | 0 | 0 |
| 350 | 60 | 0.047 | 9.6 | 9.4 | 97.1 | 2.9 | 0 | 0 | 0 | 0 |
| 350 | 30 | 0.024 | 14.7 | 20.6 | 78.6 | 7.0 | 0 | 0 | 14.3 | 0 |
| 375 | 90 | 0.071 | 14.7 | 19.2 | 66.3 | 15.1 | 0 | 0 | 16.3 | 2.3 |
| 375 | 60 | 0.047 | 15.4 | 26.8 | 62.7 | 16.3 | 0 | 0 | 18.4 | 2.6 |
| 375 | 30 | 0.024 | 24.6 | 46.6 | 51.7 | 20.3 | 0 | 0 | 23.2 | 4.8 |
| 400 | 90 | 0.071 | 25.2 | 40.5 | 57.3 | 17.7 | 2.4 | 0 | 19.8 | 2.9 |
| 400 | 60 | 0.047 | 34.3 | 60.4 | 46.9 | 20.8 | 3.9 | 0 | 24.4 | 4.1 |
| 400 | 30 | 0.024 | 39.6 | 100 | 35.8 | 21.8 | 5.2 | 0 | 26.8 | 10.3 |

Example 2

In a test for thermal reactions, wall effects, and activity of packing materials, runs were performed as in Example 1, above, however, now using a reactor loaded only with packing materials, i.e., 30–50 mesh alpha-alumina and quartz wool.

Essentially no conversion of methane or oxygen was observed at 400° C. at 30–60 mL/min feed rates.

Discussion

As essentially no conversion of methane or oxygen was observed in Example 2 using the same reactor but now loaded only with packing materials, the conversions observed in Example 1 are unaffected by wall effects.

Example 3

Deactivation of the crystalline copper aluminum borate catalyst was tested during a 19 hr run using a 2.5 g loading of the crystalline copper aluminum borate catalyst of Example 1 at 400° C. In addition, the same feed terial was gelled by adding ammonium hydroxide and methanol to obtain a final pH of 8.2. The gel was dried and calcined for 4 hr at 760° C. The calcined material was ground and sieved to 20–35 mesh prior to testing for methane chlorination. The catalyst had the X-ray diffraction pattern shown in Table I and the significant X-ray diffraction lines set forth in Table A, above.

This catalyst was tested for methane chlorination by the procedure described above in Example 1. The results for a run at a temperature of 350° C. are given below in Table IV.

TABLE IV

| Feed Rate (mL/min) at RT & 1 atm) | $CH_4$ Conv. | $O_2$ Conv. | Mole % Selectivities for Carbon-Containing Products | | | | | |
|---|---|---|---|---|---|---|---|---|
| | | | $CH_3Cl$ | $CH_2Cl_2$ | $CHCl_3$ | $CCl_4$ | CO | $CO_2$ |
| 90 | 12.6% | 28.4% | 56.1 | 9.3 | 0 | 0 | 12.7 | 22.0 |
| 60 | 17.2% | 29.6% | 52.7 | 6.9 | 0 | 0 | 17.2 | 23.2 |

Discussion

As shown by the results in Table IV, higher levels of methane and oxygen conversion were attained in Example 4 as compared to Example 1 (see Table III). Consequently, it may be concluded that if higher activity is desired, then higher surface area forms of the catalyst material may be preferred.

Example 5

Cu(NO$_3$)$_2$—5H$_2$O (232.7 g, 100. mol) dissolved in 200 mL warm deionized water, alumina sol (2218.4 g of 6.89 wt. % Al$_2$O$_3$ sol, 1.50 mol) and boric acid (124.1 g, 2.01 mol) dissolved in 600 mL warm deionized water were placed into a large Waring blender. After blending for several minutes, a thin gel formed having a pH of 3.3. A total of 1800 mL of a solution of 20% concentrated NH$_4$OH in methanol was added to the mixture. Subsequent blending resulted in a thick gel having a pH of 7.5. The material was placed on four 35×45 cm trays and allowed to air dry and subsequently dried in a vacuum oven at 0.3 atm and 120° C. for 17 hr in flowing nitrogen. Several batches were calcined with the following program:

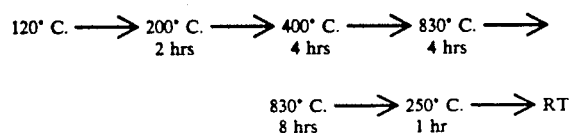

This preparation was repeated several times to obtain 143.6 g of product which was crushed and sieved to yield 20–35 mesh catalyst samples. The untreated catalyst had a BET surface area of 14 m$^2$/g, an ICP analysis of 19.8 wt. % copper, 22.6 wt. % aluminum, 7.4 wt. % boron, no detectable carbon, 0.06 wt. % hydrogen, 0.05 wt. % chlorine, and no detectable potassium and exhibited the X-ray diffraction patterns shown in Table I and the significant X-ray diffraction lines set forth in Table A, above.

Example 6

A 12.7 g sample of the 20–35 mesh copper aluminum borate prepared in Example 5 was impregnated with 1.27 g KCl dissolved in 75 mL deionized water by an incipient wetness method as follows: The KCl solution was added dropwise until an even wetness appeared. The material was allowed to dry overnight. The process was repeated 3 more times, and a final 3 mL rinse of the beaker was used for a last treatment. The material was treated at 400° C. for 6 hr. The resulting material, identified as Example 6, had a BET surface area of 10 m$^2$/g, an ICP analysis of 15.8 wt. % copper, 18.7 wt. % aluminum, 7.4 wt. % boron, 0.02 wt. % carbon, 0.09 wt. % hydrogen, 3.16 wt. % chlorine, and 3.07 wt. % potassium.

Example 7

A 13.2 g sample of the 20–35 mesh copper aluminum borate prepared in Example 5 was impregnated with 2.64 g KCl dissolved in 75 mL deionized water by an incipient wetness method as follows: the KCl solution was added dropwise until an even wetness appeared. The material was allowed to dry overnight. The process was repeated three more times, and a final 3 mL rinse of the beaker was used for a last treatment. Some white crystals appeared on the inside edge of the beaker, indicating that not all of the KCl was incorporated in the composition. The material was treated at 400° C. for 6 hr. The resulting material, identified as Example 7, had a BET surface area of 14 m$^2$/g, and an ICP analysis of 16.9 wt. % copper, 20.7 wt. % aluminum, 3.4 wt. % boron, 2.58 wt. % potassium, 3.46 wt. % chlorine and no detectable carbon or hydrogen.

Example 8

A 12.6 g sample of the 20–35 mesh copper aluminum borate prepared in Example 5 was impregnated with 1.26 g K$_2$CO$_3$ dissolved in 75 mL deionized water by an incipient wetness method as follows: the K$_2$CO$_3$ solution was added dropwise until an even wetness appeared. The material was allowed to dry overnight. The process was repeated three more times, and a final 3 mL rinse of the beaker was used for a last treatment. The material was treated in air at 600° C. for 6 hr. The resulting material, identified as Example 8, had a BET surface area of 9 m$^2$/g, and ICP analysis of 19.5 wt. % copper, 23.8 wt. % aluminum, 2.28 wt. % boron, 3.2 wt. % potassium, 0.74 wt. % chlorine and no detectable carbon or hydrogen.

Example 9

This example illustrates a comparison of the resulting catalyst of Examples 5–8 for catalytic activity in the chlorination of methane.

The catalyst testing apparatus of Example 1 was used.

Startup procedure entailed heating the catalyst charged reactor to a desired temperature and then starting a feed mixture flow, 90 mL/min measured at 1 atm and RT (corresponding to 0.071 hr$^{-1}$ methane WHSV). After 1.5-2 hr at operating conditions, a sample of reactor effluent gas was collected and GC-analyzed. Feed flow was then reduced to 60 mL/min (0.074 hr$^{-1}$ methane WHSV), and effluent was sampled after 1.5-2 hr. Feed rate was then reduced to 30 mL/min (0.024 hr$^{-1}$ methane WHSV), and effluent was sampled after 2-2.5 hr. After this sample was taken, feed was discontinued and the unit was purged with nitrogen flow overnight while raising the furnace temperature to the desired setting for the next run series.

Table V presents the results of methane chlorination runs with the catalysts of Examples 5–8.

DISCUSSION

The data in Table V illustrates that, at equivalent conversions of methane, selectivity to chloromethanes was significantly higher for potassium-containing copper aluminum borate catalysts than for comparable catalysts without potassium. Correspondingly, selectivity to carbon oxides was significantly reduced by the incorporation of potassium into the catalyst.

TABLE V

| Chlorination of Methane | | | | |
|---|---|---|---|---|
| Conditions | | Conversions | | Selectivities |
| T °C. | WHSV hr$^{-1}$ | Methane mole % | Oxygen mole % | Chlorocarbons mole % | Carbon Oxides mole % |
| Example 5 (Aqueous-Organic) | | | | | |
| 400 | 0.071 | 8.5 | 21.9 | 73.3 | 26.7 |
| 400 | 0.047 | 18.6 | 38.2 | 68.2 | 31.7 |
| 400 | 0.024 | 22.3 | 54.8 | 43.0 | 37.0 |
| 425 | 0.071 | 17.6 | 38.8 | 70.1 | 30.0 |
| 425 | 0.047 | 15.8 | 36.0 | 66.5 | 33.5 |
| 425 | 0.024 | 25.4 | 63.2 | 58.5 | 41.8 |
| Example 6 (Aqueous-Organic with 10% KCl) | | | | | |
| 400 | 0.071 | 4.7 | 11.7 | 87.7 | 12.3 |
| 400 | 0.047 | 11.1 | 19.7 | 80.3 | 19.7 |
| 400 | 0.024 | 18.8 | 34.8 | 79.6 | 20.4 |
| 425 | 0.071 | 13.9 | 22.6 | 81.7 | 18.3 |
| 425 | 0.024 | 43.7 | 50.1 | 80.6 | 19.4 |
| Example 7 | | | | | |
| 425 | 0.071 | 11.3 | 17.7 | 83.7 | 16.4 |
| 425 | 0.047 | 14.9 | 26.7 | 85.5 | 14.5 |

TABLE V-continued

| | | Chlorination of Methane | | | |
|---|---|---|---|---|---|
| | | | | Selectivities | |
| Conditions | | Conversions | | | Carbon |
| T °C. | WHSV hr$^{-1}$ | Methane mole % | Oxygen mole % | Chlorocarbons mole % | Oxides mole % |
| 425 | 0.024 | 34.1 | 56.2 | 82.5 | 17.5 |
| Example 8 | | | | | |
| 400 | 0.071 | 8.9 | 16.8 | 76.6 | 23.4 |
| 400 | 0.047 | 15.1 | 22.9 | 80.0 | 20.0 |
| 400 | 0.024 | 20.7 | 42.3 | 80.4 | 19.6 |
| 425 | 0.071 | 16.7 | 29.2 | 83.8 | 16.2 |
| 425 | 0.047 | 19.3 | 36.4 | 82.1 | 17.9 |
| 425 | 0.024 | 31.9 | 63.6 | 79.7 | 20.3 |

Example 10

A gallium-modified borosilicate sieve catalyst having the significant X-ray diffraction lines set forth in Table II was prepared by treating a granular hydrogen form borosilicate sieve material (HAMS-1B containing 0.65 wt. % boron) with GaCl$_3$ vapor at high temperature, i.e., 460° C. Subsequently, the material was water washed at room temperature to remove remaining Cl, and dried. The gallium-modified borosilicate sieve catalyst contained 5% by weight Ga and 160 ppm B, and had a BET surface area of 254 m$^2$/g.

Example 11

Ga-AMS/alumina catalyst having the significant X-ray diffraction lines set forth in Table II was prepared by mixing gallium-modified borosilicate molecular sieve material (the preparation of which is described above in Example 10) with alumina sol (PHF brand), then gelling the mixture by the addition of ammonium hydroxide. The gel was dried at 120° C., extruded to form ⅛ inch extrudates and calcined at 500° C. The calcined ⅛ inch extrudates consisted of 40 wt. % Ga-AMS and 60 wt. % PHF alumina binder. The 40 wt. % Ga-AMS/alumina contained 2 wt. % Ga.

Example 12

AMSAC-3400 catalyst having the significant X-ray diffraction lines set forth in Table II containing 40 wt. % borosilicate sieve material and 60 wt. % alumina binder in the form of 1/16 inch extrudates was calcined in air at 500° C.

Example 13

Metal-exchanged AMSAC-3400 catalysts were prepared using 20-35 mesh AMSAC-3400 of Example 12. AMSAC-3400 catalyst (20 grams) was added to a 250 mL aqueous solution of the metal nitrate (36 g ferric nitrate nonahydrate, or 23 g zinc nitrate hexahydrate) and the mixture was stirred on a Rotovap at 80° C. for 1 hour. The catalyst was collected by filtration and washed with water (3×250 mL), and the exchange procedure (1 hour at 80° C.) was repeated using a fresh metal nitrate solution. The catalyst was then washed, dried at 120° C., and calcined in flowing air at 500° C. Elemental (ICP) analyses were obtained (with percents referring to wt. %):

Fe-AMSAC-3400: 29.6% Fe, 15.8% Si, 10.5% Al, 0.10% B

Comparative Example 1

ZSM-5/alumina catalyst was prepared in the form of 80 wt. % hydrogen form ZSM-5 sieve/20 wt. % alumina binder (⅛" pellets, sieve Si/Al ratio ~30) by mixing the ZSM-5 sieve material with alumina sol, followed by gelation with ammonium hydroxide, drying, pelletizing and calcining at 500° C.

Comparative Example 2

A gallosilicate sieve material was prepared hydrothermally (e.g., the synthesis was performed in aqueous solution and at elevated temperature similarly to the ZSM-5/alumina catalyst of Comparative Example 1 and employing gallium nitrate in place of the aluminum compound) in granular form and contained 3 wt. % Ga, 35 wt. % Si, and 300 ppm Al. This catalyst was sieved to 20-35 mesh and calcined in air at 500° C. prior to use.

Examples 14-18 and Comparative Examples 3 and 4

In Examples 14-18 and Comparative Examples 3 and 4, the materials of Examples 10-13, as well as HAMS-1B borosilicate sieve material (0.65 wt. % boron), in addition to the materials of Comparative Examples 1 and 2 respectively, were tested as catalysts for the conversion of chlorocarbons using methyl chloride to simulate the feed to a reactor, such as the reactor 14, as shown in the FIGURE.

In these examples and comparative examples, a fixed-bed, single-pass stainless steel reactor unit was used. Feed gas flows were controlled by mass flow controllers. Catalyst beds were supported with stainless steel helices and quartz wool packing materials. The reactor was a 16" long, ⅜" OD ss tube with a ⅛" thermowell and was operated in downflow mode. Heating was supplied by a 12" long, three-zone tube furnace. A catalyst charge of 10.0 grams was centered in the heated portion of the reactor. The methyl chloride (Matheson, 99.5%) flow rate employed was 2.0 WHSV (160 mL/min at 1 atm and 22° C.). All experiments were performed at 1 atm pressure. The unit was configured so that reactor effluent passed directly to a gas washing bottle filled with 450 mL of 6N NaOH. The purpose of the NaOH bottle, which was maintained at about 0° C., was to immediately neutralize the HCl reaction product and to condense organic liquid (C$_5$+) product. Uncondensed gases then passed to a wet test meter and to vent. Gas sampling was performed manually at a point between the NaOH bottle and the WTM.

Table VI presents the results of methyl chloride conversion runs, which runs were all begun at the specified operating temperatures, with the first set of runs made at 300° C. (Note: All reported run temperatures are internal catalyst bed temperatures measured using thermowell in the reactor interior. Catalyst bed temperatures were reasonably uniform throughout the length of the bed, usually varying by less than 5° C. from the desired value. Also note that furnace temperature settings were slightly lower than the catalyst bed temperatures due to the exthermicity of the reaction.) After initiating methyl chloride flow, a 2-hour period was allowed for reactor line-out and saturation of the NaOH solution with effluent gases. Organic condensate was removed from the NaOH scrubber, and a 4-hour sample period was initiated. At the end of this period gas sampling was performed and the liquid organic product (condensate in the NaOH bottle) was collected and weighed. The unit was purged with N$_2$ flow overnight, the temperature was raised, and the next day a similar CH₃Cl run was performed at 350° C. Runs at 400° C. were performed on the following day after another overnight N₂ purge. Gas samples were analyzed for CH₃Cl and other organics using a Flame Ionization Detector (FID) GC. Since HCl was not quantified, conversions and mass balances were calculated using the assumption that one mole of HCl is generated for every mole of reacted CH₃Cl. Mass balances thus calculated were typically from 95-105% (weight of total effluent, including HCl, divided by feed weight).

The results are presented in Table VI below.

TABLE VI

Conversion of Methyl Chloride Over Molecular Sieve Catalysts

| Ex. | Catalyst | 300° C. | 350° C. | 400° C. |
|---|---|---|---|---|
| | | Initial CH₃Cl Conversion (%) | | |
| 14 | Ga-AMS, 5 wt. % Ga | 63 | 81 | — |
| 15 | Ga-AMS/alumina (40 wt. % Ga-AMS) | 45 | 60 | 58 |
| 16 | AMSAC-3400 | 30 | 38 | 35 |
| 17 | Fe-AMSAC-3400 (30 wt. % Fe) | 65 | 60 | — |
| 18 | HAMS-1B | <5 | <10 | — |
| C3 | ZSM-5/alumina (80 wt. % ZSM-5) | 38 | 64 | 83 |
| C4 | Gallosilicate sieve, 3 wt. % Ga | 30 | 59 | 78 |
| | | C₅+ (%) Hydrocarbon Selectivity | | |
| 14 | Ga-AMS, 5 wt. % Ga | 71 | 62 | — |
| 15 | Ga-AMS/alumina (40 wt. % Ga-AMS) | 62 | 51 | 32 |
| 16 | AMSAC-3400 | 61 | 55 | 37 |
| 17 | Fe-AMSAC-3400 (30 wt. % Fe) | 69 | 61 | — |
| 18 | HAMS-1B | — | — | — |
| C3 | ZSM-5/alumina (80 wt. % ZSM-5) | 58 | 51 | 51 |
| C4 | Gallosilicate sieve, 3 wt. % Ga | 55 | 56 | 50 |

DISCUSSION

The results in Table VI clearly indicate that the gallium-incorporated borosilicate catalysts (Ex. 14 and Ex. 15) were substantially more active for methyl chloride conversion than the HAMS-1B sieve material (Ex. 18). In addition, the catalysts of Ex. 14 and Ex. 15 were markedly more active than AMSAC-3400 (Ex. 16). Also, the Fe-AMSAC catalyst (Ex. 17) was much higher in activity than unmodified AMSAC-3400.

The results in Table VI also show that the activities of the gallium- and iron-promoted borosilicate catalyst compositions, (Ga-AMS, Ga-AMS/alumina, and Fe-AMSAC-3400) compare favorably to those of ZSM-5 (Comparative Ex. 3) and the gallosilicate sieve (Comparative Ex. 4), with the gallium and iron-promoted borosilicate catalyst compositions of the invention generally providing superior initial CH₃Cl conversions and C₅+ hydrocarbon selectivities than the catalyst materials of the comparative examples, particularly in conjunction with operation at lower temperatures, such as operation at temperatures less than 400° C., e g., operation at a temperature of about 350° C. and especially operation at a temperature of about 300° C.

It is to be understood that while the invention has been described above with reference to chlorination as the form of halogenation using the hydrogen halide, HCl (where "hydrogen halide" generally refers to HX, where X=F, Cl, Br and I), the invention, as identified above, is also believed to have applicability to hydrocarbon halogenation using other members of the halogen family, such as fluorine and iodine and, in particular, bromine and the corresponding hydrogen halide.

The foregoing detailed description is given for clearness of understanding only, and no unnecessary limitations are to be understood therefrom, as modifications within the scope of the invention will be obvious to those skilled in the art.

What is claimed is

1. A method for converting lower alkanes to higher molecular weight hydrocarbons, said method comprising the steps of:
    contacting a first reaction mixture comprising lower alkanes, a hydrogen halide and an oxygen-containing gas with a first catalytic composition comprising crystalline copper aluminum borate at appropriate reaction conditions to form an intermediate composition comprising halogenated alkanes; and
    contacting said halogenated alkanes with a second catalytic composition comprising a pentasil molecular sieve material under appropriate reaction conditions to form a product mixture comprising hydrocarbons having molecular weights greater than said lower alkanes.

2. The method of claim 1 wherein said first catalytic composition additionally comprises a promoting amount of an alkali metal compound.

3. A method of claim 2 wherein the alkali metal of said compound of said first catalytic composition is selected from the group consisting of lithium and potassium.

4. The method of claim 1 wherein said pentasil molecular sieve material comprises crystalline aluminosilicate.

5. The method of claim 1 wherein said pentasil molecular sieve material comprises silicalite.

6. The method of claim 1 wherein said hydrogen halide comprises HBr, wherein said halogenated alkanes of said intermediate composition comprise brominated alkanes.

7. The method of claim 1 wherein said lower alkanes comprise methane and said hydrogen halide comprises HCl, wherein said halogenated alkanes of said intermediate composition comprise chloromethane.

8. The method of claim 7 wherein said chloromethane comprises methyl chloride.

9. The method of claim 1 wherein said pentasil molecular sieve material comprises a borosilicate material having the following composition in terms of mole ratios of oxides:

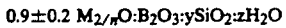

$$0.9 \pm 0.2\ M_{2/n}O:B_2O_3:ySiO_2:zH_2O$$

wherein M is at least one cation having a valence n, y is between 4 and about 600, and z is between 0 and about 160 and having the significant X-ray diffraction pattern set forth in Table I.

10. The method of claim 9 wherein said second catalytic composition additionally comprises an inorganic oxide intimately admixed with said molecular sieve material.

11. The method of claim 9 wherein said second catalytic composition additionally comprises a promoter material of at least one element selected from the group consisting of iron and gallium.

12. A method for converting methane to higher molecular weight hydrocarbons, said method comprising the steps of:

contacting a first reaction mixture comprising methane, HCl and an oxygen-containing gas with a first catalytic composition comprising crystalline copper aluminum borate, having the significant X-ray diffraction pattern set forth in Table A, at appropriate reaction conditions to form an intermediate composition comprising chloromethane; and contacting said chloromethane with a second catalytic composition under appropriate reaction conditions to form hydrocarbon products having molecular weights greater than said methane, said second catalytic composition comprising crystalline borosilicate and a porous refractory inorganic oxide, said borosilicate and said inorganic oxide having been intimately admixed with one another, said borosilicate comprising a molecular sieve material having the following composition in terms of mole ratios of oxides:

$$0.9 \pm 0.2\ M_{2/n}O:B_2O_3:ySiO_2:zH_2O$$

wherein M is at least one cation having a valence n, y is between 4 and about 600, and z is between 0 and about 160 and having the significant X-ray diffraction pattern set forth in Table II.

13. The method of claim 12 wherein said first catalytic composition additionally comprises a promoting amount of alkali metal compound.

14. The method of claim 13 wherein the alkali metal of said compound of said first catalytic composition is selected from the group consisting of lithium and potassium.

15. The method of claim 12 wherein said chloromethanes contacted with said second catalytic composition consist essentially of methyl chloride wherein said method additionally comprises the step of separating methyl chloride from the balance of said intermediate composition.

16. The method of claim 12 wherein said second catalytic composition additionally comprises an iron promoter material.

17. The method of claim 12 wherein said second catalytic composition comprises a gallium promoter material.

18. A method for converting methane to higher molecular weight hydrocarbons, said method comprising the steps of:

contacting a reaction mixture comprising methane, HCl and an oxygen-containing gas with a first catalytic composition comprising crystalline copper aluminum borate and a promoting amount of alkali metal compound, said first catalytic composition having the significant X-ray diffraction pattern set forth in Table A and having a surface area in the range of about 0.1 to about 300 m²/g, under appropriate conditions to form an intermediate composition comprising chloromethane, wherein said chloromethane comprises methyl chloride, and water; and contacting said methyl chloride with a second catalytic composition under appropriate conditions to form a product stream comprising hydrocarbons having a higher molecular weight than methane, said second catalytic composition comprising crystalline borosilicate, a porous refractory inorganic oxide and additionally comprising a promoter material of at least one element selected from the group consisting of iron and gallium, said borosilicate and said inorganic oxide having been intimately admixed with one another, said borosilicate comprising a molecular sieve material having the following composition in terms of mole ratios of oxides:

$$0.9 \pm 0.2\ M_{2/n}O:B_2O_3:ySiO_2:zH_2O$$

wherein M is at least one cation having a valence n, y is between 4 and about 600, and z is between 0 and about 160 and having the significant X-ray diffraction pattern set forth in Table II.

19. The method of claim 18 additionally comprising the step of separating said water from said intermediate composition.

20. The method of claim 18 wherein said intermediate composition additionally comprises unreacted HCl and wherein said method additionally comprises the step of separating unreacted HCl from said intermediate composition.

21. The method of claim 18 wherein intermediate composition comprises chlorocarbons in addition to methyl chloride and wherein said method additionally comprises the step of separating said chlorocarbons other than methyl chloride from said intermediate composition.

22. The method of claim 18 wherein said product stream additionally comprises HCl and said method additionally comprising the step of recycling HCl to said reaction mixture.

* * * * *